United States Patent [19]

Leander et al.

[11] Patent Number: 4,788,216
[45] Date of Patent: Nov. 29, 1988

[54] MEDICINAL USES FOR PODOPHYLLOTOXINS

[75] Inventors: Kurt Leander, Neuchâtel, Switzerland; Börje Rosén, Karlstad, Sweden

[73] Assignee: Conpharm AB, Karlstad, Sweden

[21] Appl. No.: 908,801

[22] PCT Filed: Dec. 20, 1985

[86] PCT No.: PCT/SE85/00541
§ 371 Date: Aug. 28, 1986
§ 102(e) Date: Aug. 28, 1986

[87] PCT Pub. No.: WO86/04062
PCT Pub. Date: Jul. 17, 1986

[30] Foreign Application Priority Data

Dec. 28, 1984 [SE] Sweden ............................ 8406660

[51] Int. Cl.⁴ .............................................. A61K 31/34
[52] U.S. Cl. ...................... 514/468; 549/298
[58] Field of Search .................... 549/298; 514/468

[56] References Cited

U.S. PATENT DOCUMENTS 4,122,092 10/1978 Kende et al. .............. 549/298
4,567,253 6/1986 Durst et al. .............. 549/298

FOREIGN PATENT DOCUMENTS 635769 1/1962 Canada ................. 549/298

OTHER PUBLICATIONS

Gensler et al., J. Org. Chem. 1966, vol. 31, pp. 4004–4008, 3224–3226.
Gensler et al., J.A.C.S., vol. 82, 1960, pp. 6074–6081.
Kuramochi et al., CA 104:61623t.

*Primary Examiner*—Jane T. Fan
*Attorney, Agent, or Firm*—Birch, Stewart, Kolasch & Birch

[57] ABSTRACT

The invention relates to compounds consisting of podophyllotoxin and its derivatives of the formula

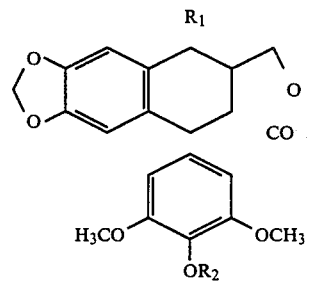

wherein $R_1$ is H or OH and $R_2$ is H or $CH_3$, for treatment of psoriasis, malaria and rheumatoid arthritis and to a method for their preparation. Furthermore, the invention concerns the use of the compounds for treatment of said states of illness, as well as the use of said compounds for the preparation of pharmacological compositions for the treatment of said states of illness.

5 Claims, No Drawings

MEDICINAL USES FOR PODOPHYLLOTOXINS

This invention relates to pharmacologically active compounds. Moreover, the invention concerns pharmacological preparations containing the compounds as well as the use of the compounds in the treatment of various diseases.

The compound according to the invention consists of podophyllotoxin and derivatives thereof which have the formula

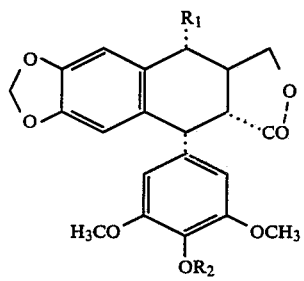

wherein $R_1$ is H or OH and $R_2$ is H or $CH_3$.

Podophyllotoxin and its derivatives have been found to have a plurality of outstanding pharmacological effects. Thus, they supress the activity of lymphatic T-cells ("killer cells") and can therefore be used to counteract reactions of immunity and rejection at transplantations. Besides, they inhibit cell division in the meta phase and can therefore be used for treatment of psoriatic diseases. The compounds also have biocidal and biostatic effects against such microorganisms as plasmodia, fungi and viruses, and they can therefore be used in the treatment of parasitic diseases, such as malaria, and viral diseases. Furthermore the compounds also act as anthelmintics.

The compound podophyllotoxin is previously known and has been extracted from plants, mainly from the genus Podophyllum. However, the compound has not earlier been used in its highly pure form according to the present invention, which has made possible its use in new indication fields. In previous works, an impure extract from Podophyllum species, so-called "podophyllin", has mostly been used, which has only contained 20–40% of podophyllotoxin. Moreover, the extract contains a great number of other components such as desoxypodophyllotoxin, dehydropodophyllotoxin, α- and β-peltatin etc., depending on from which species the extract has been recovered. Several of these other components have been found to be considerably mutagenic.

The compound podophyllotoxin has the following physical data in its pure state:

Melting point: 183°–184° C. (substance free of solvent).

Optical rotation $[\alpha]^{20}_D$: −132.5 (C0.2CHCl$_3$).

Solubility in water: 120 mg/l.

Podophyllotoxin and its derivatives can be extracted from plant parts, especially roots or rhizomes, from various species of the genus Podophyllum, such as *P. emodi Wall.* and *P. peltatum L.* The compound also occurs in other plant species, for example of the genus Juniperus such as *J. virginiana L.*

In the preparation of highly pure podophyllotoxin or its derivatives according to the invention, dried and finely ground rhizomes of e.g. Podophyllum emodi or Podophyllum peltatum are extracted e.g. with ethyl acetate and the extract is concentrated and filtered through silica gel. The desired fraction of podophyllotoxin and derivatives thereof is thereafter chromatographed on acid alumina and yields a fraction substantially containing the five lignanes deoxypodophyllotoxin, podophyllotoxone, isopicropodophylline, podophyllotoxin and 4'-demethylpodophyllotoxin. Podophyllotoxin or another desired derivative is isolated from this mixture through a careful chromatography on silica gel, after which the desired fraction is recrystallized.

Highly pure podophyllotoxin and its derivatives accordidng to the invention have been found to have a number of excellent pharmacological effects and can be used against several diseases. In accordance with this, the present invention also comprises pharmacological preparations which are characterized in that they contain podophyllotoxin and/or its derivatives together with one or more pharmacologically acceptable carrier materials.

As carrier materials all those materials can be used which are known to be useful in the preparation of pharmacological preparations, provided they do not react unfavourably with the active compound or exert some unsuitable effect together therewith. The pharmacological preparations can be made for enteral, parenteral or dermal administration and they can for example be in the form of solid preparations such as tablets, powder, capsules, suppositories or vagitories, more or less semi-liquid preparations such as ointments, gels or creams, or liquid preparations such as solutions, suspensions or emulsions. They may also contain additional conventional additives and also other therapeutically active agents. It is within the knowledge of one skilled in the art to prepare a suitable composition when the way of administration and other conditions for the administration are known.

The dose used can be established by one skilled in the art starting from conventional criteria such as the seriousness of the illness, the way of administration, the patient's age and condition, etc.

Podophylloytoxin and its derivatives according to the invention can be used for the treatment of a number of different diseases which ca be summarized into the following groups. Non-restrictive examples are given for each group.

1. Tropical diseases such as malaria and schizotomiasis.
2. Skin diseases such as psoriasis, fungal infections and alopecia areata.
3. Reactions of rejection at transplantations.
4. Collagenoses (connective tissue diseases) such as rheumatoidal arthritis, systemic lupus erythematosus disseminatur, sclerodermy, polyartheritis nodosa and sarcoidosis.
5. Mental illness (caused by virus) such as demens and psychoses.
6. Neurological diseases such as multiple sclerosis and myasthenia gravis.

The therapeutic effects on the diseases mentioned above are based on a number of acting mechanisms of podophyllotoxin and its derivatives. Firstly, the compounds inhibit the activity of lymphatic T-cells (so-called "killer cells") which is of importance to counteract reactions of rejection at transplantations. Furthermore, the compounds counteract cell division in the metaphase which is of a great importance at certain skin diseases such as psoriatic states. The compounds have also a biocidal or biostatic effect against such microorganisms as plasmodia, fungi and viruses, whereby a plurality of diseases caused by microorganisms as well as malaria can be treated. Finally, the compounds have also anthelmintic properties ad can thus be used as agents against helminths and other parasites.

Thus, in accordance with another aspect of the invention, it also comprises a method of treating states of illness caused by activity of the disease agents mentioned above and is characterized in that one or more of the compounds or a pharmacological preparation according to the invention is furnished to the organism attacked by the illness.

The organisms attacked by said illnesses may be humans or animals.

Podophyllotoxin and its derivatives according to the invention have been subjected to a number of pharmacological, toxicological and clinical investigations in order to establish their therapeutic properties. The results of these investigations are described in the following.

ACUTE TOXICITY

The acute toxicity of podophyllotoxin has been determined on various test animals and by various ways of administration. The results appear from the following table 1.

TABLE 1

| Test animal | Way of Administration | Acute toxicity $LD_{50}$ mg/kg |
|---|---|---|
| Rat | i.v. | 10 |
| Mouse | i.v. | 20 |
| Mouse | p.o. | 100 |
| Rat | dermal | 500 |
| Rabiit | dermal | 200 |

EFFECT AGAINST MALERIA

The effect against malaria was determined clinically on a number of patients which had been attacked by the malaria parasite *Plasmodium falciparum*. Podophyllotoxin was administered in two different doses and the number of parasites in the patients was determined for each day and was noted as the number of asexual parasites per cubic millimeter of blood. The results appear from the following table 2.

very strong requires a cooperation between different cell types, substantially macrophages, T and B lymphocytes, and can easily be detected in the spleen of the test animals. This reaction can be inhibited in a dose-dependent way by daily injections of podophyllotoxin after administration of erythrocytes.

A transplantation of skin to genetically different mice normally leads to a rejection within 10 days. It has been found in many cases that a markedly prolonged time of survival of 15 days and longer is obtained with animals treated with a compound according to the invention as compared with an untreated control group.

At investigations in vitro, it has also been found that podophyllotoxin inhibits the proliferation of cells caused by mitrogenic lectins or cells from a non-related individual and also inhibits the development of cytotoxic cells. However, at markedly lower doses these effects increase. Other investigations show that cells treated with podophyllotoxin could recover complete reactivity to these stimuli within 24 hours.

EFFECT AGAINST PSORIASIS

A clinical investigation was carried out with totally 152 patients of an age between 19 and 71 years (mean value 46.1 years) afflicted with psoriasis vulgaris. The patients were divided into three groups of 50, 51 and 51 persons who were treated topically with a cream containing 0.1, 0.25 and 0.5% of podophyllotoxin, respectively. Each patient was treated only on a specific attacked area of the body while other attacked areas served as comparison. The severity of the attack was judged at the start of the treatment, and 2, 4, 8, 12 and 16 weeks after this, no treatment being carried out during the last period of 4 weeks. The investigation was carried out with double blind technique and the results were treated statistically.

At all three dosage levels, statistically significant improvements ($p<0.001$) were obtained regarding the severity of the treated lesions with associated symptoms. As early as after a treatment time of two weeks, there was a statistically significant difference ($p<0.001$) between treated and untreated lesions, and this difference increased in the course of the treatment. At the fifth control, 70–75% of the patients were free from symptoms or had only mild ones, while only two of the patients showed the corresponding improvements for

TABLE 2

| Dose | Patient No. | Day 0 | 1 | 2 | 3 | 4 | 5 | 6 | 7 | Remarks |
|---|---|---|---|---|---|---|---|---|---|---|
| 1.5 mg per day (t.i.d.) | 1 | 660 | 180 | 0 | 0 | 180 | 270 | 270 | 270 | Marked reduction of parasites at the start - the patient later treated with chloroquine |
| | 2 | 13710 | 3000 | 120 | 0 | 0 | 0 | 0 | 0 | Cured |
| | 4 | 1410 | 360 | 0 | 0 | 60 | 60 | 60 | 60 | P. Disappeared on day 2 but reappeared |
| | 5 | 960 | 90 | 0 | 0 | 0 | 0 | 0 | 0 | Cured |
| | 6 | 13080 | 510 | 0 | 0 | 0 | 0 | 0 | 0 | Cured |
| | 7 | 4380 | 1560 | 180 | 660 | 1400 | — | — | — | Fell ill - treated with chloroquine |
| 3.0 mg per day (t.i.d.) | 3 | 2880 | 2520 | 60 | 540 | 600 | 600 | 0 | 0 | Cured |
| | 8 | 2060 | 1600 | 60 | 0 | 0 | 0 | 0 | 0 | Cured |
| | 9 | 6080 | 2000 | 0 | 0 | 0 | 0 | 0 | 0 | Cured |
| | 10 | 320 | 60 | 0 | 0 | 0 | 0 | 0 | 0 | Cured |

EFFECT AGAINST REACTIONS OF IMMUNITY AND REJECTION

Injection with a suspension of erythrocytes from sheep to mice causes formation of specific antibodies against this antigen. This reaction which normally is the untreated lesions. In the follow-up time, weeks 13 to 16, no deterioration occurred as to the severity or symptoms of the treated lesions. Only 11 of the patients reported any secondary effects such as rash. These secondary effects disappeared after interruption of the treatment. Differences between the three treated groups regarding the number of cases with secondary effects are not statistically significant (p about 0.50).

We claim:

1. A method of treating psoriasis which comprises administering to a host in need thereof, an antipsoriasis effective amount of a compound having the formula:

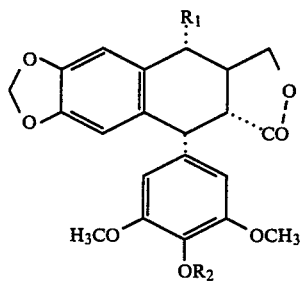

wherein $R_1$ is H or OH and $R_2$ is H or $CH_3$.

2. A method of treating malaria by administering to a host in need thereof an antimalarial effective amount of the compound having the formula

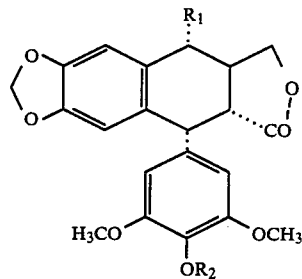

wherein $R_1$ is H or OH, and $R_2$ is H or $CH_3$.

3. A method of treating rheumatoid arthritis by administering to a host in need thereof an antiarthritis effective amount of the compound having the formula

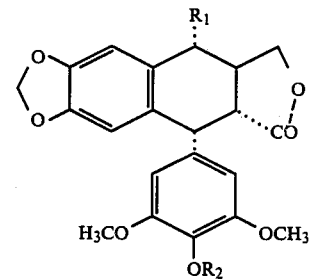

wherein $R_1$ is H or OH and $R_2$ is H or $CH_3$.

4. The method according to claim 2 wherein said antimalarial effective amount is from about 1.5 to 3.0 mg/day.

5. The method according to claim 1 wherein said antipsoriasis effective amount is present in an amount of from 0.1% to 0.5% by weight.

* * * * *